United States Patent [19]

Fanta et al.

[11] Patent Number: 4,483,950

[45] Date of Patent: Nov. 20, 1984

[54] MODIFIED STARCHES AS EXTENDERS FOR ABSORBENT POLYMERS

[75] Inventors: George F. Fanta, Peoria; William M. Doane, Morton, both of Ill.; Edward I. Stout, Shawnee Mission, Kans.

[73] Assignee: The United States of America as represented by the Secretary of Agriculture, Washington, D.C.

[21] Appl. No.: 448,675

[22] Filed: Dec. 10, 1982

[51] Int. Cl.³ ............................ C08L 3/02; C08L 3/04
[52] U.S. Cl. ........................................ 524/48; 524/47; 525/54.32; 526/238.22
[58] Field of Search ...................... 524/47, 48, 50, 51; 527/309; 526/238.22; 525/54.32

[56] References Cited

U.S. PATENT DOCUMENTS

| | | | |
|---|---|---|---|
| 3,935,099 | 1/1976 | Weaver et al. | 210/43 |
| 3,985,616 | 10/1976 | Weaver et al. | 525/54.32 |
| 3,997,484 | 12/1976 | Weaver et al. | 525/54.32 |
| 4,069,177 | 1/1978 | Smith | 526/238.22 |
| 4,116,899 | 9/1978 | Fanta et al. | 525/54.32 |

*Primary Examiner*—John Kight
*Assistant Examiner*—Nathan M. Nutter
*Attorney, Agent, or Firm*—M. Howard Silverstein; David G. McConnell; Curtis P. Ribando

[57] ABSTRACT

Starch-based superabsorbents are extended by blending with highly modified, low molecular weight starches. The dextrinized starches synergistically interact with the superabsorbents thereby permitting dilution without a commensurate reduction in the water absorbency. While the principal utility of the blends is the absorption of aqueous fluids, when hydrated they yield soft, smooth gels useful as high-quality thickening agents.

10 Claims, No Drawings

MODIFIED STARCHES AS EXTENDERS FOR ABSORBENT POLYMERS

BACKGROUND OF THE INVENTION

1. Field of the Invention

Polymeric substances which have the ability to absorb large amounts of aqueous fluids are well known in the prior art and are typically referred to as "superabsorbents." Starch-based superabsorbents are particularly useful, and are easily prepared by first graft polymerizing either acrylonitrile or mixtures of monomers that contain predominantly acrylonitrile onto either starch or flour and then, in a second step, saponifying the polyacrylonitrile moiety by treating the graft copolymer with hot alkali. This process has been reviewed by Fanta and Bagley in the *Encyclopedia of Polymer Science and Technology*, Supplement Vol. 2 (H. F. Mark and N. M. Bikales, eds., John Wiley & Sons, 1977, p. 665). There are a multitude of uses for superabsorbents. For example, they are used in agriculture to increase the water-holding capacity of poor or marginal soils, as seed coatings to enhance germination, and as root dipping compositions to reduce or eliminate transplant shock. Superabsorbents find application in disposable soft goods, such as diapers and feminine napkins, for enhancing the absorbtivity of these articles toward body fluids. Another important use for these substances is as thickening agents for aqueous systems. Medical applications include incorporation into body powders and wound dressings, particularly for the treatment of decubitus ulcers or bed sores.

Although superabsorbents enjoy a broad fluid of application, their cost is often an inhibiting factor in their widespread commercial acceptance, particularly in agriculture. Diluting the absorbent with an inexpensive extender, such as starch, has obvious marketing advantages. However, it is at once apparent that addition of an inert diluent will decrease the water absorbency of the resulting blend in an amount proportional to the amount of diluent added. This invention relates to diluting superabsorbents without a proportionate sacrifice of absorbency.

2. Description of the Prior Art

In U.S. Pat. No. 3,935,099 and related U.S. Pat. Nos. 3,981,100, 3,985,616, and 3,997,484, Weaver et al. teach that absorbent polymers may be extended by mixing dispersions of the saponified, gelatinized starch-polyacrylonitrile graft copolymers (GS-HPAN) with dispersions of inexpensive natural polymers, or their derivatives, and then drying the resulting mixtures. Exemplary extenders include flour, guar, gelatin, starch and dextrin. In Example 20 and accompanying Table 9, Weaver et al. illustrate the expected diluent effect on absorbency of several of these extenders.

SUMMARY OF THE INVENTION

We have now surprisingly discovered that selected modified starches, particularly those whose molecular weights have been significantly reduced may be used to extend superabsorbents without a commensurate reduction in the water absorbency of the resulting blended compositions. This behavior is totally unexpected in view of the drastic reduction in absorbency observed upon extension with unmodified starch or the acid-modified flour of Weaver et al. We have also discovered that the physical properties of the water-solution gels obtained from the instant blends are superior in certain applications to those resulting from nondiluted absorbents.

In accordance with this discovery, it is an object of the invention to provide more economical absorbent compositions by diluting GS-HPAN polymers with inexpensive extenders.

It is also an object of the invention to extend GS-HPAN polymers by blending with dextrinized starches which synergistically enhance the absorbency of the polymers. In the preferred embodiments, blends comprising up to 50% of selected dextrins display water absorbencies comparable to the undiluted absorbent.

Another object of the invention is to provide extended absorbent compositions which yield soft, smooth gels having application as high-quality thickening agents.

Other objects and advantages of this invention will become readily apparent from the ensuing description.

DETAILED DESCRIPTION OF THE INVENTION

It is well known that modification of starch by treatment with acid or enzyme causes a lowering in the molecular weight of the polysaccharide and provides a starch composition which is more water soluble than its unmodified precursor. Increases in acid concentration, reaction temperature, and reaction time will decrease the polysaccharide molecular weight and increase its water solubility.

The modified starches for use in the invention are comparatively low molecular weight dextrins resulting from relatively extensive acid or enzyme treatment. Indicative of the molecular weight is inherent viscosity as determined by the standard procedure of Myers et al. in *Methods in Carbohydrate Chemistry* (Vol. IV, R. L. Whistler, ed., Academic Press, 1964, pp. 124–127, herein incorporated by reference). Dextrins having inherent viscosities in the range of about 0.05 to 0.60 dl./g. at 0.5% (w/v) in 1N NaOH are considered to be within the scope of the invention, with those having viscosities in the range of 0.05 to 0.25 dl./g. being preferred. By comparison, the inherent viscosity of unmodified starch is approximately 2.3 dl./g.

The specific source of the starch intended for dextrinization is not especially critical and may include any of the common cereal grains such as corn, wheat, and rice, or the root crops as exemplified by potato and tapioca. It is important, however, that the starch be separated from the nonamylaceous components which would otherwise tend to interfere with the absorbency of the blended compositions. Substantially pure starch fractions obtained from conventional grain wet milling or root crop processing operations are suitable.

The extenders contemplated herein may be advantageously combined with any of the previously discussed starch-based superabsorbents; namely, those which are prepared by graft polymerizing acrylonitrile or mixtures of monomers that contain predominantly acrylonitrile onto either starch or flours, and then saponifying the resultant product. In the course of the superabsorbent preparation, it is critical that the extender be incorporated into the aqueous dispersion of the starch-graft copolymer prior to the final drying step. Typically, it will be added in the sequence step either immediately preceding or immediately after saponification. At the time of addition, the extender may be in a dry powdered state or in the form of an aqueous dispersion. Upon thorough mixing of the components, the saponified and neutralized blend is dried by any conventional means to a moisture content in the range of about 1-15% water by weight.

The aforementioned modified starch extenders have little or no absorbent capacity of their own, generally less than about 1 g. water/1 g. extender. However, when blended in combination with superabsorbents in amounts of up to about 2 parts extender:1 part absorbent on a dry weight basis, they exhibit a significant synergistic behavior. Blends comprising highly modified starch extenders with inherent viscosities in the preferred range of 0.05 to 0.25 dl./g., and having a ratio of extender:absorbent of 1:2, and in some cases as much as 1:1, are characterized by absorbencies closely approximating those of the undiluted absorbent. The water solubility of the instant blends will be a function of both the degree of extender modification and its level of addition.

Gels prepared from the blended absorbents are characterized by a soft, smooth texture. This quality renders the products of the invention particularly well suited for use as thickening agents for aqueous systems, where a grainy, particulate character would be objectionable. The gels become softer and smoother as the degree of modification of the diluent increases. This tailoring of superabsorbent quality by simple dilution is a facile alternative to the precipitation process of the prior art.

The following examples are intended only to further illustrate the invention and are not intended to limit the scope of the invention which is defined by the claims.

EXAMPLE 1

This example illustrates one method for the synthesis of the saponified starch-polyacrylonitrile graft copolymer (GS-HPAN) reaction mixture useful in the blends of the instant invention.

A 10-cu.-ft. ribbon blender was charged with 33.25 lb. of unmodified wheat starch and 400 lb. of water, and the stirred slurry was heated for 30 min. at 86°-90° C. After the mixture was cooled to 32° C., 34.5 lb. of acrylonitrile was added, followed after 2 min. by a solution of 354.2 g. of ceric ammonium nitrate in 8 l. of water containing 42 ml. of concentrated nitric acid. After the mixture had stirred at 32°-45° C. for 40 min., it was neutralized with 45% potassium hydroxide solution, and the unreacted acrylonitrile was removed by azeotropic distillation. Fifty pounds of water and 47 lb. of 45% potassium hydroxide solution was then added to the dispersion of starch-PAN graft copolymer, and the saponification was carried out by heating the mixture for about 2.5 hr. at 90°-95° C., while allowing the ammonia formed in the reaction to vent to the atmosphere. The alkaline GS-HPAN reaction mixture was stored at 4° C.

EXAMPLES 2A-2E

To 50 g. of the GS-HPAN reaction mixture of Example 1 (19.1% solids, pH 9.6) was added 10 g. (dry basis) of either a commercial corn starch or a commercial acid-modified starch (dextrin). The mixture was kneaded to thoroughly blend the powdered starch or dextrin with the GS-HPAN dough. Glacial acetic acid was then kneaded into the blend to adjust the pH to 7.2-7.4. The resulting blends were then drum dried on an 18×12 in. double drum drier that was heated with 58 p.s.i.g. steam and was rotated at 4 r.p.m. Absorbencies of drum-dried products were obtained by allowing an accurately weighed sample (2-10 mg.) to soak in distilled water for 30 min. The swollen gel was separated from unabsorbed water by pouring the dispersion through a tared 280 mesh sieve and allowing it to drain for 20 min. Absorbency, in grams of water per gram of polymer, was calculated from the weight of water-swollen gel and the weight of sample used for the test. Solubilities of drum-dried products were obtained by allowing a known weight of sample to stand overnight in a known weight of water. After removal of the gel fraction by filtration, a known weight of the clear filtrate was freeze dried, and the solubility was calculated based upon the weight of the solid residue.

Table I compares the absorbencies and water solubilities of a number of drum-dried GS-HPAN products extended with acid-modified starches (white dextrins) having a range of inherent viscosities to drum-dried, nonextended GS-HPAN and to the drum-dried GS-HPAN extended with the corn starch. The expected absorbency of each of the extended products based upon the percentage of GS-HPAN present was 215 g./g., representing a variation from the control of −51%. The actual variation from the control for each of the dextrin-extended products was significantly less than expected. That for the starch-extended product was actually more than expected. The product of Example 2E gave a softer, smoother gel than the others when hydrated for the absorbency test, and consequently it was not as thoroughly drained on the sieve. This factor may have contributed to the absorbency value being higher than that of the control.

TABLE I

| Example No. | Extender | GS-HPAN, % by wt. | Inherent viscosity | Drum-dried product | | |
|---|---|---|---|---|---|---|
| | | | | Water solubility, % | Absorbency, g./g. | Variation from control, % |
| 2A | none (control) | 100 | — | 34 | 440 | — |
| 2B | corn starch | 49 | 2.308 | 21 | 140 | −68 |
| 2C | white dextrin c | 49 | 0.590 | 64 | 310 | −30 |
| 2D | white dextrin d | 49 | 0.326 | 76 | 380 | −14 |
| 2E | white dextrin e | 49 | 0.057 | 76 | 500 | +14 |

EXAMPLE 3

To 50-g. samples of the GS-HPAN reaction mixture of Example 1 were added either 5 g., 10 g., or 20 g. (dry basis) of the dextrin used in Example 2E. Samples were prepared, drum dried, and tested for absorbency as described in Examples 2A-2E. As noted for Example 2E, samples gave soft, smooth gels when placed in water, and complete separation from unabsorbed water was difficult. Results are given in Table II.

EXAMPLE 4

To 50-g. samples of the GS-HPAN reaction mixture of Example 1 were added either 5 g., 10 g., or 20 g. (dry basis) of the dextrin used in Example 2D. Samples were prepared, drum dried, and tested for absorbency as described in Examples 2A–2E, and results are given in Table III.

EXAMPLE 5

To 50-g. samples of the GS-HPAN reaction mixture of Example 1 were added either 5 g., 10 g., or 20 g. (dry basis) of corn starch. Samples were prepared, drum dried, and tested for absorbency as described in Examples 2A–2E, and results are given in Table IV. As indicated by a comparison of the actual and expected variations from the control, the unmodified starch extender actually had a slight negative effect on the GS-HPAN absorbency, beyond the effect attributed to dilution.

It is understood that the foregoing detailed description is given merely by way of illustration and that modification and variations may be made therein without departing from the spirit and scope of the invention.

product, a dextrin extender characterized by an inherent viscosity in the range of about 0.05 to 0.60 dl./g. at 0.5% (w/v) in 1N NaOH; and b. drying the saponified blend to a moisture content of from about 1 to 15% water by weight.

2. A method as described in claim 1 wherein said blending step is prior to saponification.

3. A method as described in claim 1 wherein said blending step is subsequent to saponification.

4. A method as described in claim 1 wherein said dextrin is characterized by an inherent viscosity in the range of 0.05 to 0.25 dl./g.

5. A method as described in claim 1 wherein the ratio of said extender to said starch graft copolymer reaction product on a dry weight basis is in the range of 1:2 to 2:1.

6. A method as described in claim 1 wherein the ratio of said extender to said starch graft copolymer reaction product on a dry weight basis is in the range of 1:2 to 1:1.

7. An extended starch-based superabsorbent material prepared by the method of claim 1.

8. An extended starch-based superabsorbent material prepared by the method of claim 4.

TABLE II

| Example No. | Amount of dextrin e extender, g. | GS-HPAN, % by wt. | Drum-dried product | | | |
|---|---|---|---|---|---|---|
| | | | Absorbency, g./g. | | Variation from control, % | |
| | | | Actual | Expected | Actual | Expected |
| 3A | none (control) | 100 | 360 | — | — | — |
| 3B | 5 | 66 | 440 | 236 | +22 | −34 |
| 3C | 10 | 49 | 340 | 176 | −6 | −51 |
| 3D | 20 | 32 | 200 | 116 | −44 | −68 |

TABLE III

| Example No. | Amount of dextrin d extender, g. | GS-HPAM, % by wt. | Drum-dried product | | | |
|---|---|---|---|---|---|---|
| | | | Absorbency, g./g. | | Variation from control, % | |
| | | | Actual | Expected | Actual | Expected |
| 4A | none (control) | 100 | 410 | — | — | — |
| 4B | 5 | 66 | 390 | 268 | −5 | −34 |
| 4C | 10 | 49 | 320 | 200 | −22 | −51 |
| 4D | 20 | 32 | 260 | 159 | −37 | −68 |

TABLE IV

| Example No. | Amount of starch extender, g. | GS-HPAN % by wt. | Drum-dried product | | | |
|---|---|---|---|---|---|---|
| | | | Absorbency, g./g. | | Variation from control, % | |
| | | | Actual | Expected | Actual | Expected |
| 5A | none (control) | 100 | 370 | — | — | — |
| 5B | 5 | 66 | 230 | 243 | −38 | −34 |
| 5C | 10 | 49 | 140 | 181 | −62 | −51 |
| 5D | 20 | 32 | 72 | 120 | −81 | −68 |

We claim:

1. A method for preparing an extended starch-based superabsorbent material comprising:
   a. blending into an aqueous dispersion of a gelatinized starch-graft copolymer reaction product, either prior to or subsequent to saponification of said 9. An extended starch-based superabsorbent material prepared by the method of claim 5.

10. An extended starch-based superabsorbent material prepared by the method of claim 6.

* * * * *